(12) United States Patent
Oka et al.

(10) Patent No.: US 10,688,133 B2
(45) Date of Patent: Jun. 23, 2020

(54) CELL SHEET COMPOSITION FOR INHIBITING PROGRESSION OF RENAL DISORDER, METHOD OF PRODUCING THE SAME, AND METHOD OF INHIBITING PROGRESSION OF RENAL DISORDER USING THE SAME

(71) Applicant: TOKYO WOMEN'S MEDICAL UNIVERSITY, Tokyo (JP)

(72) Inventors: Masatoshi Oka, Tokyo (JP); Sachiko Sekiya, Tokyo (JP); Tatsuya Shimizu, Tokyo (JP); Kosaku Nitta, Tokyo (JP); Teruo Okano, Tokyo (JP)

(73) Assignee: TOKYO WOMEN'S MEDICAL UNIVERSITY, Tokyo (JP)

( * ) Notice: Subject to any disclaimer, the term of this patent is extended or adjusted under 35 U.S.C. 154(b) by 0 days.

(21) Appl. No.: 15/415,708

(22) Filed: Jan. 25, 2017

(65) Prior Publication Data
US 2017/0216362 A1   Aug. 3, 2017

(30) Foreign Application Priority Data

Jan. 29, 2016   (JP) ................................. 2016-016546

(51) Int. Cl.
| | | |
|---|---|---|
| A61K 35/545 | (2015.01) | |
| C12N 5/07 | (2010.01) | |
| A61K 35/28 | (2015.01) | |
| A61L 27/38 | (2006.01) | |
| C07K 14/00 | (2006.01) | |
| C07K 14/475 | (2006.01) | |
| C12N 5/0775 | (2010.01) | |
| A61K 38/18 | (2006.01) | |
| C12N 5/00 | (2006.01) | |
| A61K 48/00 | (2006.01) | |
| A61K 35/12 | (2015.01) | |

(52) U.S. Cl.
CPC .......... *A61K 35/28* (2013.01); *A61K 38/1833* (2013.01); *A61L 27/3804* (2013.01); *A61L 27/3839* (2013.01); *C07K 14/00* (2013.01); *C07K 14/4753* (2013.01); *C12N 5/0068* (2013.01); *C12N 5/0663* (2013.01); *A61K 48/00* (2013.01); *A61K 2035/124* (2013.01); *C12N 2501/12* (2013.01); *C12N 2510/00* (2013.01)

(58) Field of Classification Search
None
See application file for complete search history.

(56) References Cited

U.S. PATENT DOCUMENTS

| | | | | |
|---|---|---|---|---|
| 2003/0064088 A1* | 4/2003 | Carvalho | ................... | A61F 2/02 424/423 |
| 2004/0028657 A1* | 2/2004 | Okano | ................... | A61L 27/362 424/93.7 |
| 2013/0101659 A1* | 4/2013 | Sawa | ................... | A61L 27/367 424/443 |
| 2013/0171213 A1* | 7/2013 | Sekine | ................ | C12N 5/0657 424/400 |

FOREIGN PATENT DOCUMENTS

| | | |
|---|---|---|
| CN | 101837014 A | 9/2010 |
| WO | 2011/058813 A1 | 5/2011 |
| WO | WO2012036224 * | 3/2012 |

OTHER PUBLICATIONS

Chen et al. Stem Cell Dev 2011;20:103-113.*
Liu et al. J Pediatric Surg 2011;46:537-45.*
Vukicevic et al., Effects of 1a,25- and 24R,25-Dihydroxyvitamin D3 on Aluminum-Induced Rickets in Growing Uremic Rats; 1987; Journal of Bone and Mineral Research; pp. 533-545.*
Gao et al., "Hepatocyte growth factor gene therapy retards the progression of chronic obstructive nephropathy," Kidney International, 2002, vol. 62, pp. 1238-1248.
Mizuno et al., "Hepatocyte growth factor suppresses interstitial fibrosis in a mouse model of obstructive nephropathy," Kidney International, 2001, vol. 59, pp. 1304-1314.
Sugiura et al., "Pharmacokinetic Modeling of Hepatocyte Growth Factor in Experimental Animals and Humans," Journal of Pharmaceutical Sciences, Jan. 2013, vol. 102, No. 1, pp. 237-249.
Oka et al., "Renal fibrosis suppression effect by local HGF administration using transplantation of HGF-secreting cell sheet onto kidney," Regenerative Medicine, 2015, vol. 14 Suppl., p. 255, O-47-3.

* cited by examiner

*Primary Examiner* — Maria G Leavitt
(74) *Attorney, Agent, or Firm* — Kilpatrick Townsend & Stockton LLP

(57) ABSTRACT

The present invention provides a method of inhibiting progression of or preventing renal disorder, the method comprising applying a cell sheet composition for inhibiting progression of or preventing renal disorder to at least one part of the surface of a kidney, wherein the part of the surface is uncovered by a fibrous capsule of the kidney. The present invention also provides a cell sheet composition for inhibiting progression of or preventing renal disorder, the cell sheet composition comprising a cell that has a function of producing a hepatocyte growth factor (HGF). The present invention also provides a method of producing a cell sheet composition for inhibiting progression of or preventing renal disorder.

6 Claims, 8 Drawing Sheets

Specification includes a Sequence Listing.

CELL SHEET COMPOSITION FOR INHIBITING PROGRESSION OF RENAL DISORDER, METHOD OF PRODUCING THE SAME, AND METHOD OF INHIBITING PROGRESSION OF RENAL DISORDER USING THE SAME

TECHNICAL FIELD

The present invention relates to a cell sheet composition for inhibiting progression of or preventing renal disorder. This cell sheet composition comprises a cell that has a function of producing a hepatocyte growth factor (HGF). The present invention also relates to a method of producing a cell sheet composition for inhibiting progression of or preventing renal disorder. The present invention further relates to a method of inhibiting progression of or preventing renal disorder using a cell sheet composition. This application claims the priority of Japanese Patent Application No. 2016-016546, filed to the JPO on Jan. 29, 2016, the entire disclosure of which is incorporated herein by reference.

BACKGROUND ART

Chronic kidney disease (CKD) results from diseases including diabetes and hypertension. In CKD, renal fibrosis progresses gradually and irreversibly, leading to an eventual loss of renal functions. CKD patients are diagnosed with end-stage renal disease when the condition progresses to a point where only 15% or less of renal functions remains. Treatment of end-stage renal disease requires renal replacement therapy and often requires hemodialysis as well. Hemodialysis therapy has the following problems: it takes several hours per session, about three sessions per week, which leads to a significant decrease in quality of life (QOL); it induces complications when the therapy continues for a prolonged period of time; and it incurs high medical expenses for life-long treatment, which has become a social issue. To avoid the need for hemodialysis or peritoneal dialysis therapy, patients with end-stage renal disease require kidney transplantation. However, there is a serious shortage of kidney donors worldwide including in Japan, and therefore these conventional therapies need to be replaced by a new one. It is an urgent matter to inhibit the progression of CKD conditions for reducing the frequency of conducting dialysis therapy.

Attempts have been made to inhibit CKD progression by treating the primary diseases. However, no direct treatment of the kidneys themselves has been established. Cytokines such as an HGF were studied for their action to inhibit progression of renal fibrosis (NPLs 1 and 2, for example). However, the cytokines are lost upon systemic administration by substantial proportions due to first-pass effect in the liver, making it difficult to retain effective concentrations of the cytokines to act on the kidneys for an extended period of time (NPL 3).

CITATION LIST

Non Patent Literature

[NPL 1] Mizuno S., Matumoto K., Nakamura T., Kidney Int. 1304-1314 2001
[NPL 2] Gao X., Mae H., Ayabe N., et al. Kidney Int. 1238-1248 2002
[NPL 3] Sugiura T., Takahashi S., Sano K., et al. Journal of Pharmaceutical Science 237-249 2013

SUMMARY OF INVENTION

Technical Problem

As described above, no therapeutic agent or method that has been developed so far can adequately inhibit CKD progression. An object of the present invention is to provide a cell sheet composition for inhibiting progression of or preventing renal disorder. Another object of the present invention is to provide a method of producing a cell sheet composition for inhibiting progression of or preventing renal disorder. Yet another object of the present invention is to provide a method of inhibiting progression of or preventing renal disorder using a cell sheet composition.

Solution to Problem

The inventors of the present invention have conducted research and development from various angles to achieve these objects. As a result, they have unexpectedly found that a cell sheet composition comprising a cell that has a function of producing a hepatocyte growth factor (HGF) inhibits progression of or prevents renal disorder when applied to a kidney. The present invention provides the following:

[1] A cell sheet composition for inhibiting progression of or preventing renal disorder, the cell sheet composition comprising a cell that has a function of producing a hepatocyte growth factor (HGF).

[2] The cell sheet composition according to [1] applicable to at least one part of a surface of a kidney, wherein the part of the surface is uncovered by a fibrous capsule of the kidney.

[3] The cell sheet composition according to [1] or [2], wherein the renal disorder results from one or more kidney diseases selected from the group consisting of diabetic nephropathy, nephrosclerosis, chronic glomerulonephritis, IgA nephropathy, obstructive nephropathy, rapidly progressive glomerulonephritis, lupus nephritis, interstitial nephritis, and post-kidney-transplantation nephropathy.

[4] The cell sheet composition according to any one of [1] to [3], wherein the cell comprises a cell having a vector having a nucleic acid encoding an HGF protein.

[5] The cell sheet composition according to any one of [1] to [5], wherein the cell comprises a mesenchymal stem cell.

[6] The cell sheet composition according to [5], wherein the mesenchymal stem cell is derived from cord blood, placenta, bone marrow, adipose tissue, a synovial membrane, dental pulp, and/or a pluripotent stem cell.

[7] The cell sheet composition according to [5], wherein the mesenchymal stem cell is derived from bone marrow.

[8] A method of producing the cell sheet composition set forth in any one of [1] to [7], the method comprising:
(1) seeding a group of cells on a stimulus-responsive cell culture substrate and culturing the cells to confluency, the cells comprising a cell that has a function of producing a hepatocyte growth factor (HGF); and
(2) giving the stimulus-responsive cell culture substrate a stimulus to induce detachment of the cells from the substrate.

[9] The method according to [8], wherein a medium used in culturing in step (1) contains ascorbic acid or a salt thereof.

[10] A method of inhibiting progression of or preventing renal disorder, the method comprising applying the cell sheet composition set forth in any one of [1] to [7] to a surface of a kidney of a mammal under a fibrous capsule of the kidney.

[11] A method of inhibiting progression of or preventing renal disorder in a subject in need of treatment of the renal disorder, the method comprising applying a cell sheet composition to a kidney of the subject, the cell sheet composition comprising a cell that has a function of producing a hepatocyte growth factor (HGF).

[12] The method according to [11], wherein the cell sheet composition is applied to at least one part of a surface of the kidney of the subject, wherein the part of the surface is uncovered by a fibrous capsule of the kidney.

[13] The method according to [11], wherein the renal disorder results from one or more kidney diseases selected from the group consisting of diabetic nephropathy, nephrosclerosis, chronic glomerulonephritis, IgA nephropathy, obstructive nephropathy, rapidly progressive glomerulonephritis, lupus nephritis, interstitial nephritis, and post-kidney-transplantation nephropathy.

[14] The method according to [11], wherein the cell comprises a cell having a vector having a nucleic acid encoding an HGF protein.

[15] The method according to [11], wherein the cell comprises a mesenchymal stem cell.

[16] The method according to [15], wherein the mesenchymal stem cell is derived from cord blood, placenta, bone marrow, adipose tissue, a synovial membrane, dental pulp, and/or a pluripotent stem cell.

[17] The cell sheet composition according to [15], wherein the mesenchymal stem cell is derived from bone marrow.

Advantageous Effects of Invention

The present invention can remarkably inhibit progression of renal fibrosis resulting from various causes and therefore retain renal functions. The present invention also alleviates vascular insufficiency occurring in the renal medulla due to kidney disorder; retains the structure of renal tubules in the renal medulla, in which the renal tubules are responsible for one of the most important renal functions, urine concentration (water reabsorption), and are also responsible for functions of a living organism to regulate electrolyte concentrations and pH and reabsorb proteins and amino acids; and remarkably alleviates degradation of renal medullary functions and thinning of renal parenchyma caused by collapse of the renal medullary structure. The present invention can inhibit or prevent CKD progression, reduce the number of patients who start hemodialysis therapy, and contribute to QOL improvement and significant reduction in medical cost.

DESCRIPTION OF EMBODIMENTS

Figure 1:
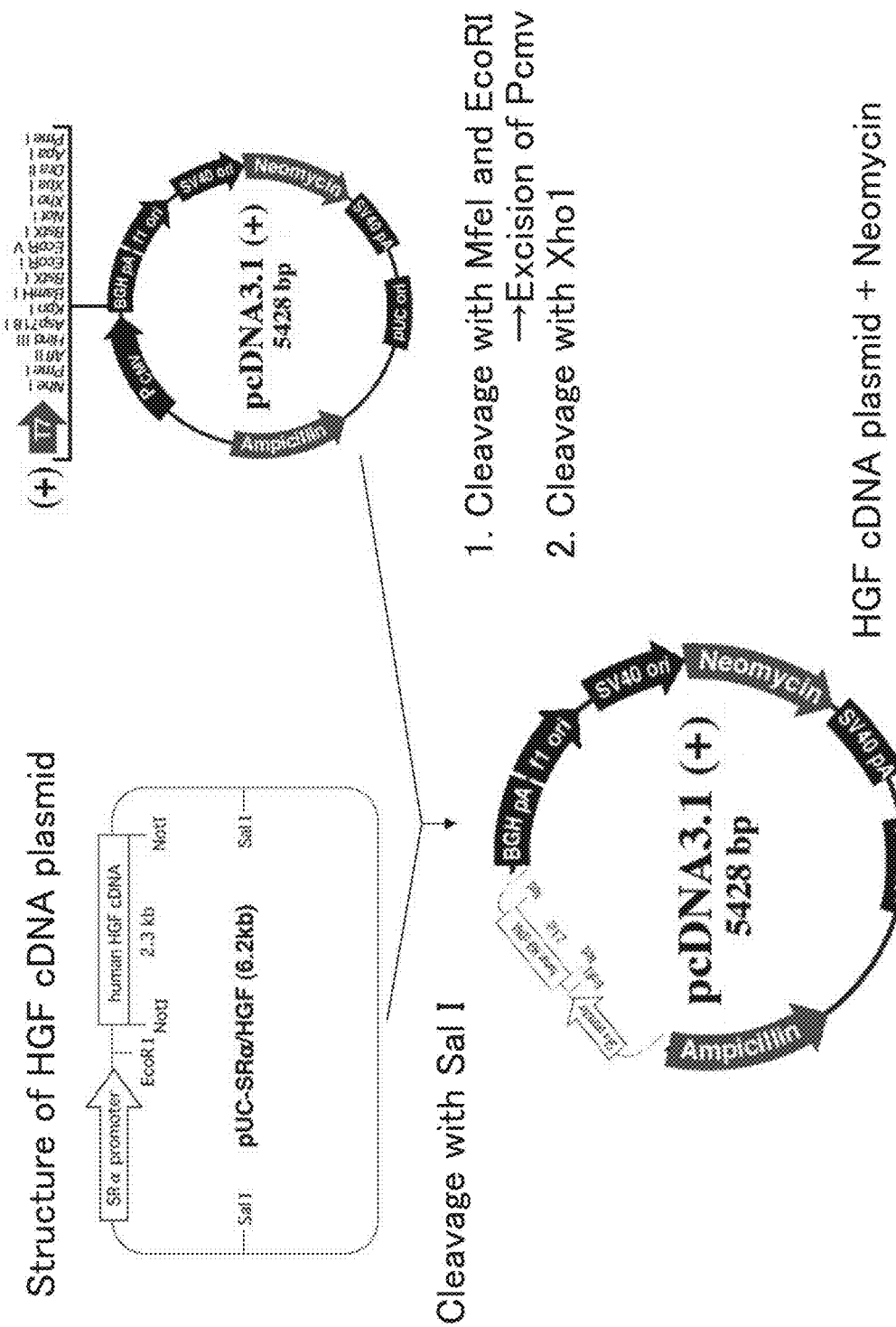
FIG. 1 illustrates a procedure for constructing a vector for expression of a hepatocyte growth factor (HGF) protein.

Broadly speaking, kidneys are important urinary organs that remove waste products from the blood, filtrate out and discharge water, and retain body fluid homeostasis. A pair of kidneys develops from the mesoderm, and they sit in the back of the abdomen below the diaphragm in a human body. Histologically, a kidney comprises the parenchyma consisting of the cortex and the medulla. The cortex has many functional units called nephrons, and about two million nephrons are present in the left and right human kidneys. Each nephron is composed of a renal corpuscle and a renal tubule extending from the renal corpuscle. The renal corpuscle is composed of an afferent arteriole; a glomerulus, which is a tuft of capillaries that are the branched ends of the afferent arteriole; and an efferent arteriole, which is the extension of the glomerular capillaries merged again into a single tube. Surrounding the glomerulus is Bowman's capsule, which receives toxic-material-containing water filtrated off the capillaries. Bowman's capsule communicates with a renal tubule. Nephrons perform filtration, reabsorption, secretion, and concentration and produce urine.

It is known that approximately one in eight Japanese adults and 25 million Americans have chronic kidney disease (CKD). CKD develops from many diseases such as diabetes, hypertension, and chronic glomerulonephritis. CKD diagnosis is made when nephropathy is apparent from manifestation of abnormal urine such as proteinuria (including microalbuminuria), diagnostic imaging, blood tests, and/or pathological finding, or when the glomerular filtration rate (eGFR) remains lower than 60 mL/minute/1.73 $m^2$ for three months or longer (KDIGO (Kidney Disease: Improving Global Outcome) "clinical practice guideline for the evaluation and management of chronic kidney disease" 2012). CKD is classified into G1 to G5 based on the degree of progression, in which CKD becomes more serious as the number increases. A wide range of researches demonstrates that patients with advanced CKD have a low glomerular filtration rate and renal interstitial fibrosis in common. Fibrosis refers to sclerosis of an organ or tissue due to accumulating extracellular matrix molecules such as collagen excessively in the organ or tissue caused by a disorder of the organ or tissue. Progression of fibrosis causes dysfunction of the organ. In the kidneys, progression of fibrosis causes a gradual loss of the urine-producing and regulatory functions of the kidneys, and severe fibrosis is fatal unless any of hemodialysis, peritoneal dialysis, and kidney transplantation is performed. Since renal fibrosis progresses irreversibly, the only way to offset the loss of renal functions under current circumstances is hemodialysis, peritoneal dialysis, or kidney transplantation. It is therefore important to inhibit progression of renal fibrosis to retain renal functions.

As nephropathy progresses, the intrarenal blood flow slows down; the renal medullary structure irreversibly collapses; renal medullary functions degrade; and renal parenchyma becomes thinner. The renal medulla is an important piece of tissue that is responsible for urine concentration (water reabsorption) and also for functions of a living organism to regulate electrolyte concentrations and pH and reabsorb proteins and amino acids. In order to retain renal functions, it is important not only to inhibit progression of fibrosis of the renal cortex but also to inhibit collapse of the renal medullary structure, degradation of renal medullary functions, and/or thinning of the renal parenchyma.

The term "renal disorder" used herein refers to fibrosis of the renal cortex, collapse of the renal medullary structure, degradation of renal medullary functions, and/or thinning of the renal parenchyma, as described above. The phrase "progression of renal disorder" used herein refers to the progression of fibrosis of the renal cortex, collapse of the renal medullary structure, degradation of renal medullary functions, and/or thinning of the renal parenchyma, as described above. The present invention can inhibit progression of or preventing renal disorder and therefore retain renal functions.

Examples of the renal disorder to which the present invention is applicable include diabetic nephropathy, nephrosclerosis, chronic glomerulonephritis, IgA nephropathy, obstructive nephropathy, rapidly progressive glomerulonephritis, lupus nephritis, interstitial nephritis, and post-kidney-transplantation nephropathy. Progression of the conditions of the renal disorder causes fibrosis of the renal cortex, collapse of the renal medullary structure, degradation of renal medullary functions, and/or thinning of the renal parenchyma. The present invention can inhibit or prevent fibrosis of the renal cortex, collapse of the renal medullary structure, degradation of renal medullary functions, and/or thinning of the renal parenchyma caused by the renal disorder.

A hepatocyte growth factor (HGF) is a cytokine typically produced by cells such as fibroblasts, macrophages, vascular endothelial cells, vascular smooth muscle cells, and mesenchymal stem cells, and is known as a factor that has a major role in controlling proliferation and functions of epithelial cells. Besides its functions to hepatic parenchymal cells, an HGF is also known to act to enhance migration capability of vascular endothelial cells, induce morphogenesis such as lumen formation, protect the cells from apoptosis, form new blood vessels, and regulate immune response, among others. The HGF is also known to have action to inhibit renal fibrosis upon systemic administration. However, an administered HGF rapidly degrades in the liver, making it difficult to retain effective concentrations of an HGF to inhibit progression of renal disorder. The present invention can achieve effective amounts of an HGF to act directly and persistently on a kidney to inhibit progression of or prevent renal disorder.

A cell that has a function of producing a hepatocyte growth factor (HGF) of the present invention may be, for example, a cell persistently expressing an HGF protein, a cell expressing an HGF protein temporarily or persistently by transfecting an HGF-gene-encoding vector, or a cell that has been activated by a certain method to endogenously express an HGF gene. A cell that produces an HGF stably and continuously is preferably used, and thus a cell expressing an HGF protein persistently or a cell expressing an HGF protein persistently by transfecting an HGF-gene-encoding vector is preferably used. Examples of the cell expressing an HGF protein persistently that is used in the present invention include mesenchymal stem cells, fibroblasts, vascular endothelial cells, vascular smooth muscle cells, and myoblasts, which may be used alone or in combination.

The phrase "cell that has a function of producing a hepatocyte growth factor (HGF)" used herein refers to a cell capable of producing an HGF protein through transcription, translation, and the like of an intracellular HGF gene in a typical culturing environment or in an in vivo environment. The phrase "cell that has a function of producing a hepatocyte growth factor (HGF)" used herein may also be defined as a cell that releases a significantly high amount of an HGF protein, compared to a cell having an HGF gene but producing no HGF protein in a typical culturing environment. The amount of an HGF protein may be measured with a commercially available ELISA kit for HGF protein assay, or by any other known approach.

The HGF gene that is introduced into a cell in the present invention preferably expresses an HGF protein of a particular animal species to which the present invention is to be applied. In the case where the animal species is humans, a human HGF having an amino acid sequence represented by SEQ ID NO:1 may be encoded in the vector for use in introduction. Besides SEQ ID NO:1, the amino acid sequence of the HGF protein to be expressed in the present invention may be an amino acid sequence encoded by a gene present in common in mammals including humans. In order to use the gene product in the present invention, a gene derived from a certain mammal (human, rat, mouse, guinea pig, marmoset, rabbit, dog, cat, sheep, pig, horse, cow, goat, monkey, or chimpanzee, for example) may also be used. Not only the wild-type genes but also an HGF-protein-expressing gene that comprises substitution, insertion, and/or deletion of several (from 1 to 10, preferably from 1 to 6, more preferably from 1 to 4, further preferably from 1 to 3, particularly preferably 1 or 2, for example) amino acids and expresses an HGF protein with functions similar to those of a wild-type HGF protein may be used.

The term "cytokine" used herein is a generic name for physiologically active trace proteins produced by cells, and is defined herein to be equivalent to this term in the broadest sense in the art. Cytokines are responsible for cell-cell communication and involved in proliferation, differentiation, and expression of functions of cells. After produced by a cell, a cytokine functions either in an autocrine fashion (to act on the same cell) or in a paracrine fashion (to act on other cells). The cell used in the present invention, which has a function of producing an HGF, may also produce a plurality of cytokines other than the HGF or may have a gene for expressing a non-HGF cytokine introduced therein. Examples of the non-HGF cytokine include cell growth factors, such as vascular endothelial growth factors (VEGFs), fibroblast growth factors (FGFs), epidermal growth factors (EGFs), bone morphogenetic factor (BMP7), and platelet-derived growth factors (PDGFs); interleukins; chemokines; hematopoietic factors, such as colony-stimulating factors; tumor necrosis factors; and interferons.

Any vector can be used without restriction for expression of an HGF protein in the present invention and may be appropriately selected. Examples of the vector include plasmid vectors, cosmid vectors, fosmid vectors, viral vectors, and artificial chromosome vectors. The HGF gene can be introduced into the vector by any recombinant DNA technique. The transfection of a cell with the vector encoding the HGF gene may also be performed by any known process. The screening of the cell having the gene introduced therein and expressing an HGF protein persistently can be performed by any process. For example, the screening may be conducted with an agent suitable for a resistance gene introduced in the vector (the agent may be neomycin or hygromycin, for example).

The term "cell sheet composition" used herein refers to a single sheet or multiple sheets composed of a group of cells comprising a plurality of certain cells. This sheet is obtained by culturing the group of cells on a cell culture substrate and then inducing the group of cells to detach from the cell culture substrate. Examples of the method of producing the cell sheet composition include the following: a method involving culture of the cells on a stimulus-responsive cell culture substrate coated with a polymer that changes its molecular structure in response to a stimulus such as temperature, pH, or light, then varying the stimulus (temperature, pH, or light) to modify the conditions of the surface of the stimulus-responsive cell culture substrate, and thereby inducing the detachment of the cells in the form of sheet from the stimulus-responsive cell culture substrate while maintaining the adhesion between the cells; and a method involving culture of the cells on any cell culture substrate and then physical detachment of the cells from an end of the cell culture substrate with tweezers or any other tool. In a preferred method, the stimulus-responsive cell culture substrate used is a temperature-responsive cell culture substrate that has a surface coated with a polymer having variable hydration force at temperatures ranging from 0° C. to 80° C. In this method, the cells are cultured on the temperature-responsive cell culture substrate at a temperature within a temperature range causing a weak hydration force in the polymer, and subsequently the temperature of a liquid culture medium in which the cells are being cultured is varied to a temperature causing a strong hydration force of the polymer, thereby induction of the cells in the form of sheet to detach from the temperature-responsive cell culture substrate. During this method, the first culturing of the cells is conducted on the cell culture substrate that has a surface coated with a polymer having variable hydration force at temperatures ranging from 0° C. to 80° C., and then this culturing is conducted at a temperature causing weak hydration force of the polymer. Preferably, the temperature range is a typical temperature range for cell culturing, for example, from 33° C. to 40° C. The temperature-responsive polymer used in the present invention may be either a homopolymer or a copolymer. Examples of the polymer include a polymer described in Japanese Patent Application Publication No. 2-211865.

For illustrative purposes, use of a temperature-responsive culture dish containing poly(N-isopropylacrylamide) as a stimulus-responsive polymer, particularly as a temperature-responsive polymer, is described below. Poly(N-isopropylacrylamide) is known to have a lower critical solution temperature of 31° C. At 31° C. or higher, free poly(N-isopropylacrylamide) in water is dehydrated and its polymer chain agglomerates, making the water turbid. At 31° C. or lower, the polymer chain is hydrated and dissolved in water. In the present invention, this polymer is used as a coating to be immobilized on the surface of a substrate such as a petri dish. At 31° C. or higher, the polymer on the surface of the cell culture substrate is dehydrated with its polymer chain being immobilized on the surface, rendering the surface hydrophobic. At 31° C. or lower, the polymer on the surface of the cell culture substrate is hydrated with its polymer chain coating the surface, rendering the surface hydrophilic. The hydrophobic surface is appropriate for adhesion and proliferation of the cells, while the hydrophilic surface does not allow adhesion of the cells thereto. Because of such characteristics, cooling the substrate to 31° C. or lower induces the cells to detach from the surface. With the cells being cultured to confluency to cover the entire culture surface, cooling the substrate to 31° C. or lower can allow harvesting a cell sheet composition. Any temperature-responsive culture dish having these effects can be used. Examples thereof include UpCell® commercially available from CellSeed Inc., Tokyo, Japan.

Examples of the animal species from which the cells used in the present invention are derived include mammals such as human, rat, mouse, guinea pig, marmoset, rabbit, dog, cat, sheep, pig, horse, cow, goat, monkey, chimpanzee, and those mammals rendered immunodeficient, avians, reptiles, amphibians, fishes, and insects. Preferably, human cells are used when the cell sheet composition of the present invention is used for treating humans; pig cells for treating pigs; monkey cells for treating monkeys; chimpanzee cells for treating chimpanzees; and cat cells for treating cats. For treatment of a human patient, the cells may be collected from the same patient (autologous cells), or may be collected from any other person (allogeneic cells), or may be a commercially available cell line.

The term "mesenchymal stem cell" used herein refers to an undifferentiated cell capable of differentiating into various mesenchymal cells such as adipocytes, chondrocytes, osteocytes, myoblasts, fibroblasts, stromal cells, and/or tenocytes, and also capable of self-renewal. The International Society for Cellular Therapy (ISCT) advocate the following three minimal criteria for defining mesenchymal stem cells: (1) mesenchymal stem cells must be cultured in contact with plastic under standard culture conditions; (2) immunologically, mesenchymal stem cells must be positive for expression of CD105, CD73, and CD90 and negative for expression of CD45, CD34, CD14 or CD11b, CD79a or CD19, and HLA-DR; and (3) mesenchymal stem cells must differentiate to osteoblasts, adipocytes, and chondroblasts in vitro. The mesenchymal stem cell of the present invention however is not restricted by these criteria. In addition to these markers, CD29, CD44, CD106, and STRO-1 are also exemplified as positive markers for mesenchymal stem cells. In the present invention, the term "mesenchymal stem cell" is used in its broadest sense to the utmost extent.

The mesenchymal stem cell can be isolated in vivo from tissue such as bone marrow, adipose tissue, cord blood, dental pulp, a synovial membrane, and placenta by any known method.

For example, a bone-marrow-derived mesenchymal stem cell can be isolated as an adherent cell by collecting bone marrow aspirate from bone marrow, separating hemocytes therefrom by density gradient centrifugation, seeding the hemocytes on a plastic culture dish, and culturing these in an environment at 37° C. and 5% $CO_2$.

For example, an adipose-derived mesenchymal stem cell (adipose-derived stem cell) can be isolated as an adherent cell by collecting and mincing adipose tissue, treating the tissue with collagenase type II at 37° C. for 1 hour for digestion, adding a medium thereto for centrifugation, rinsing precipitated cells with a basal medium, filtrating the cells through a mesh such as a cell strainer, seeding the resulting cells on a plastic culture dish, and culturing the cells in an environment at 37° C. and 5% $CO_2$. In the case where the mesenchymal stem cell is derived from other tissue, the cell may be isolated by any known method.

The mesenchymal stem-cell may be derived from a pluripotent stem cell by induced differentiation. The term "pluripotent stem cell" used herein refers to a cell having a self-renewal ability and pluripotency. Pluripotency indicates that the cell is transformable to any cell type making up the body, and the self-renewal ability indicates that a single cell can produce two undifferentiated cells identical to itself. Examples of the pluripotent stem cell used in the present invention include embryonic stem cells (ES cells), embryonal carcinoma cells (EC cells), trophoblast stem cells (TS cells), epiblast stem cells (EpiS cells), embryonic germ cells (EG cells), multipotent germline stem cells (mGS cells), induced pluripotent stem cells (iPS cells), and Muse cells (see International Publication No. WO2011/007900). The mesenchymal stem cell may be induced from the pluripotent stem cell by a known process (for example, see Japanese Patent Application Publication No. 2012-120486 and Fukuta M., et al., Derivation of mesenchymal stromal cells from pluripotent stem cells through a neural crest lineage using small molecule compounds with defined media. PLOS ONE, 2014; 9(12): e112291).

The differentiation potency of the mesenchymal stem cell may be checked by a known method. For example, the differentiation potency of the mesenchymal stem cell into an adipocyte may be checked by culturing the mesenchymal stem cell in a medium supplemented with insulin and dexamethasone and then performing Oil Red O staining. For example, the differentiation potency of the mesenchymal stem cell into an osteocyte may be checked by culturing the mesenchymal stem cell in a medium supplemented with ascorbic acid, β-glycerophosphoric acid, and dexamethasone and then performing alkaline phosphatase staining. For example, the myogenic differentiation potency of the mesenchymal stem cell may be checked by culturing the mesenchymal stem cell in a medium supplemented with horse serum and then observing for the presence of a particular fused cell formed from myocytes. The differentiation potency of the mesenchymal stem cell into other cell types may also be confirmed by any known method. The occurrence of differentiated cells may be checked by a known method, for example, by employing a technique such as real-time PCR or flow cytometry to detect a gene or a protein which is only expressed when the induced differentiation occurs.

Any source of the mesenchymal stem cell can be used in the present invention. Bone marrow or adipose tissue is preferred because the methods of collecting and separating mesenchymal stem cells from such tissue are widely established.

The mesenchymal stem cell from some sources does not readily adhere to the cell culture substrate. In this case, the cell may be cultured on a cell culture substrate coated in advance with a cell adhesion protein such as collagen, laminin, laminin 5, fibronectin, or Matrigel or with a mixture of two or more of these. The method of coating the cell adhesion protein may be a conventional method. Examples thereof include a method involving application of an aqueous solution of the cell adhesion protein to the surface of the cell culture substrate, removal of the aqueous solution from the surface, and then rinse of the surface.

In the present invention, the number of the cells having an ability to produce a hepatocyte growth factor (HGF) and contained in the cell sheet composition is not limited and varies depending on the size of the application site and the level of the ability. The proportion of the cells having an ability to produce a hepatocyte growth factor (HGF) in the cell sheet composition of the present invention is not limited and may be 30% or higher, 40% or higher, 50% or higher, 55% or higher, 60% or higher, 65% or higher, 70% or higher, 75% or higher, 80% or higher, 85% or higher, 90% or higher, 93% or higher, 95% or higher, 97% or higher, 98% or higher, or 99% or higher, for example. A higher proportion of the cells having an ability to produce a hepatocyte growth factor (HGF) in the cell sheet composition leads to stronger effects of inhibiting or preventing fibrosis of the renal cortex, collapse of the renal medullary structure, degradation of renal medullary functions, and/or thinning of the renal parenchyma.

In an embodiment of the present invention, the cell in the cell sheet composition may further comprise a cell other than the mesenchymal stem cell. Examples of the other cell include vascular endothelial cells, vascular endothelial progenitor cells, fibroblasts, epithelial cells, and stromal cells, which may be appropriately selected depending on the site for transplantation and the purpose of transplantation. The cell in the cell sheet composition may further comprise another cell (for example, a mesenchymal cell) derived from the same tissue serving as the source of the mesenchymal stem cell.

In the present invention, the number of cells to seed for preparing the cell sheet composition varies depending on the animal species and the cell type, and may range from $0.3 \times 10^4$ cells/cm$^2$ to $10 \times 10^6$ cells/cm$^2$, from $0.5 \times 10^4$ cells/cm$^2$ to $8 \times 10^6$ cells/cm$^2$, or from $0.7 \times 10^4$ cells/cm$^2$ to $5 \times 10^6$ cells/cm$^2$, for example. In the present invention, detachment of the cell sheet composition from the temperature-responsive cell culture substrate is induced by raising the temperature of the cell culture substrate that has the cell adhering thereto in a state of confluency or subconfluency, to a temperature equivalent to or higher than the upper-limit critical dissolution temperature of the coating polymer or to a temperature equivalent to or lower than the lower-limit critical dissolution temperature of the coating polymer. The cell sheet composition may be prepared in a liquid culture medium or in other isotonic solutions, depending on the purpose. For quick and highly efficient detaching and harvesting of the cell sheet composition, one of or a combination of the following methods may be adopted: gentle tap or sway of the cell culture substrate; stirring of the medium with a pipette; and use of tweezers. The culture conditions other than the temperature may be selected according to a conventional procedure. For example, the medium may be a known medium supplemented with a serum such as fetal bovine serum (FBS) or may be a serum-free medium.

The form of the cell culture substrate for preparation of the cell sheet composition used in the present invention may be a dish, a Multiwell Plate, a flask, or a flat membrane, for example. Examples of the material of the cell culture substrate include compounds typically used for cell culturing, such as glass, modified glass, polystyrene, poly(methyl methacrylate), and polycarbonates; and typical formable substances, such as polymer compounds other than those described above and ceramics.

The cell culture substrate for preparation of the cell sheet composition used in the present invention may have both an area to which cells adhere and an area to which no cells adhere, on the culture surface. For example, use of a cell culture substrate having both a plurality of circular cell-adhesion areas and a non-cell-adhesion area occupying the rest of the culture surface enables a plurality of cell sheets to be prepared at once. The shape of the cell-adhesion area may be circular, square, triangular, or rectangular, for example, and may be desirably selected depending on the purpose. The size of the cell-adhesion area may also be appropriately determined. The non-cell-adhesion area can be provided by any method. Examples thereof include formation of coating with non-cell-adhesion polymers having low affinity to cells, such as hydrophilic polymers, such as poly(N-acryloylmorpholine), polyacrylamide, polydimethylacrylamide, poly(ethylene glycol), and cellulose; and highly hydrophobic polymers, such as silicone polymers and fluoropolymers.

The cell sheet composition of the present invention is obtained without a protease such as dispase or trypsin, which is conventionally used for harvesting adherent cells. Thus, the cell sheet composition of the present invention has little damage on proteins expressed on the cell surfaces. For this reason, the bottom plane of the cell sheet composition after detached from the cell culture substrate (in other words, the plane once in contact with the cell culture substrate) has many undamaged adhesion proteins on it and retains cell-cell desmosome structures. With these cell-cell desmosome structures retained, the cell sheet composition is suitable for apply to an affected area of a living organism and for stacking one another. Dispase is a protease known to have action to make cells detached while retaining from 10% to 40% of the cell-cell desmosome structures. However, dispase also destroys other molecules such as basement-membrane-like proteins that are present between a cell and a cell culture substrate. In contrast, the cell sheet composition used in the present invention can retain at least 60% of both the desmosome structures and basement-membrane-like proteins during detachment and harvesting, providing those various effects described above.

The cell sheet composition of the present invention may be a multilayered cell sheet composition consisting of a plurality of cell sheet compositions. The multilayered cell sheet composition, when used in the present invention, has more cells to be applied to an affected area and therefore has an enhanced effect of inhibiting or preventing fibrosis of the renal cortex, collapse of the renal medullary structure, degradation of renal medullary functions, and/or thinning of the renal parenchyma. Examples of the method of obtaining the multilayered cell sheet composition include the following: drawing a cell sheet composition floating in a liquid culture medium together with some of the liquid culture medium and then dispensing the cell sheet composition onto another cell sheet composition placed in a different culture dish with a pipette or any other tool, whereby stacking the sheets by means of flow of the liquid culture medium; and stacking the sheets with a cell-transportation jig. In the present invention, the multilayered cell sheet composition is produced preferably with a cell-transportation jig because the constituent cell sheet composition can be stacked without damage. The cell-transportation jig is simply required to have a function to hold the cell sheet composition. Examples of the material for the cell-transportation jig can include poly(vinylidene difluoride) (PVDF), silicone resins, poly (vinyl alcohol), urethane, cellulose and derivatives thereof, chitin, chitosan, collagen, gelatin, and fibrin gel. The configuration of the cell-transportation jig may be a stamp, a membrane, a porous membrane, a piece of nonwoven fabric, or a piece of woven fabric, for example. The cell-transportation jig of an embodiment of the present invention is simply required to have a function to harvest the cell sheet composition without breaking it and then stack it on another cell sheet composition, and is preferably a cultured-cell transportation jig equipped with a cell adhesion part comprising one, two, or more of a cell adhesion protein, a cell adhesion peptide, and a hydrophilic polymer. For example, a stamp-type cultured-cell transportation jig equipped with a cell adhesion part is disclosed in Japanese Patent Application Publication No. 2005-176812. The cell adhesion part of this stamp-type cultured-cell transportation jig can allow harvesting a cell sheet composition without breakage of the cell sheet composition or shrinkage of the cell sheet composition from occurring upon detachment from a culture dish. The cell sheet composition can be easily transported and stacked onto another one without causing shrinkage of the cell sheet composition with this cell-transportation jig. Stacking constituent cell sheet compositions without shrinkage can provide a multilayered cell sheet composition that has a dense three-dimensional structure with no gaps between the constituent cell sheet compositions.

In the method of producing the cell sheet composition of the present invention, the culture medium may be further supplemented with ascorbic acid (see Kato Y, et al. Allogeneic Transplantation of an Adipose-Derived Stem Cell Sheet Combined With Artificial Skin Accelerates Wound Healing in a Rat Wound Model of Type 2 Diabetes and Obesity. Diabetes. 2015 August; 64(8):2723-34). Compared to a cell sheet composition comprising a mesenchymal stem cell cultured in a medium supplemented with no ascorbic acid, a cell sheet composition comprising a mesenchymal stem cell cultured in a medium supplemented with ascorbic acid is strong and does not readily break. This phenomenon occurs probably because ascorbic acid facilitates secretion of extracellular matrix molecules from cells in the cell sheet composition and these molecules make the cell sheet composition stronger. Thus, culturing in a medium supplemented with ascorbic acid is preferable for obtaining a cell sheet composition suitable for transplantation.

The term "ascorbic acid" used herein refers to ascorbic acid, a derivative thereof (ascorbyl-2-phosphate, ascorbyl-1-phosphate, or sodium L-ascorbate, for example), and a salt thereof (a sodium salt or a magnesium salt, for example).

Many organs in the abdominal cavity are each surrounded by a capsule (serosa), which holds the corresponding organ to the abdominal wall and at a certain position in the abdominal cavity. A fibrous capsule is primarily composed of a squamous epithelium monolayer (mesothelial cell). In the present invention, the cell sheet composition is preferably applied to at least one part of a surface of an organ, more preferably at least one part of a surface of an organ wherein the part of the surface is uncovered by a fibrous capsule. The cell sheet composition of the present invention applied to at least one part of a surface of an organ from which a fibrous capsule has been removed can release various cytokines including an HGF steadily and persistently toward the part, resulting in a remarkable enhancement of the effects of present invention.

EXAMPLES

The present invention will now be described in more detail by examples. The scope of the present invention, however, is not limited to these examples. The protocol for conducting experiments accompanied by use of a rat in these examples has been approved by the ethics committee for animal experiments of Tokyo Women's Medical University and was implemented according to "Guide for the Care and Use of Laboratory Animals" (revised in 1996) issued by National Institute of Health (NIH).
<Materials and Methods>
1. Method of Cell Sheet Preparation
1-1. Preparation of Cell Genetically Modified and Given HGF-Producing Function
1-1-1. Construction of Plasmid Vector for hHGF Protein Expression Genetic modification was conducted by a known genetic recombination method according to the procedure shown in FIG. 1. The procedure is summarized as follows:
(1) From a plasmid harboring a human HGF cDNA coding for an amino acid sequence represented by SEQ ID NO:1 and SRα promoter 5' upstream of the human HGF cDNA (pUC-SRα/HGF (6.2 kb), see Seki T., Hagiya M., Simonishi M., Nakamura T., Shimizu S. Organization of human hepatocyte growth factor-encoding gene. Gene 1991 Vol. 102 213-219), a nucleic acid sequence was digested with restriction enzyme SalI.
(2) From pcDNA3.1(+) (Invitrogen), $P_{CMV}$ was digested with restriction enzymes MfeI and EcoRI.
(3) A multicloning site of the pcDNA3.1(+) was treated with restriction enzyme XhoI, followed by ligation of the nucleic acid fragment obtained in (1) thereto.
1-1-2. Acquisition of HGF-Protein-Expressing Cell A cell genetically modified to have an HGF-producing function was produced by transfecting the plasmid vector for hHGF expression into a human mesothelial cell line (Met-5A, SV40 immortalized cell) through lipofection (Lipofectamine(registered trademark), Invitrogen), followed by cloning with G418. The resulting Met-HGF cell was cultured in a liquid culture medium M199 (Sigma, #M4530) supplemented with antibiotics (penicillin and streptomycin, Sigma), 0.15 mg/L Hydrocortisone (Sigma, #H6909), 5 mg/mL Insulin (Wako), 500 ng/mL G418 (Invitrogen), and 10% fetal bovine serum FBS (Japan Bio Serum) (the medium is hereinafter called "Met medium"). Met-5A, which was not transfected with the plasmid vector, was cultured and allowed to proliferate in a Met medium supplemented in the same manner as above except G418, until a necessary number of cells grew.
1-2. Preparation of Cell Sheet Using Cells Having an Introduced HGF-Gene A cell sheet was prepared as follows. Cells ($1.2 \times 10^6$) were seeded in a Met medium contained in a 35-mm temperature-responsive culture dish (UpCell®, CellSeed Inc., Tokyo, Japan). The cells were cultured in an incubator at 37° C. and 5% $CO_2$ for four days and then in an incubator at 20° C. and 5% $CO_2$ for one hour to induce the cells to detach from the culture dish. A cell sheet for inhibiting progression of renal disorder was thereby harvested.
1-3. Collection and Culture of Bone Marrow Mesenchymal Stem Cells A GFP-expressing male rat of four to six week old (SD-Tg (CAG-EGFP) Rat) was sacrificed. The femoral bone marrow aspirate was drawn with a 23G needle into a 5-mL syringe containing 10%-FBS-containing DMEM (Sigma) supplemented with antibiotics (penicillin and streptomycin, Sigma) (the medium is hereinafter called "Complete medium"). Flushing was performed twice to collect bone marrow cells. Foreign matter was removed from the cells through a cell strainer (BD Falcon). The resulting cells were centrifuged and then suspended in 10 mL of a Complete medium, followed by culturing in a 100-mm cell culture dish (BD Falcon) in an incubator at 37° C. and 5% $CO_2$ for 24 hours. After a lapse of 24 hours, the liquid culture medium was removed, and the cells were rinsed with 5 mL of PBS three times to remove contaminating erythrocytes. Culture was performed again in 10 mL of a Complete medium for four to five days to confluency, for passaging. After three rounds of passaging using trypsin and EDTA, bone marrow mesenchymal cells for preparation of a cell sheet were obtained.
1-4. Preparation of Cell Sheet Comprising Mesenchymal Stem Cells The mesenchymal stem cells ($3 \times 10^5$ to $4 \times 10^5$ cells) obtained by the procedure described above were seeded on a 35-mm temperature-responsive culture dish (UpCell(registered trademark), CellSeed Inc., Tokyo, Japan) using a Complete medium. After three days, the medium was changed to a Complete medium supplemented with 250 µg/L ascorbic acid (WAKO, #013-19641). After another three days, the medium was changed again to a Complete medium supplemented with ascorbic acid. On the next day (seven days after seeding), the cells were cultured in an incubator at 20° C. and 5% $CO_2$ for about 10 minutes for inducing the cells to detach from the culture dish. A cell sheet was thereby harvested.

2. Analysis of Effects of Cell Sheet Comprising Mesenchymal Stem Cells

2-1. Preparation of Model of Unilateral Ureteral Obstruction (hereinafter, called "UUO")

Under isoflurane anesthesia, a five-week-old male nude rat (F344/NJcl-rnu/rnu, CLEA Japan) was incised on the back just above a kidney so as to expose the kidney. Fat was gently removed from the renal hilum, exposing the ureter. The ureter was obstructed at three positions between the kidney and 5 mm away therefrom, at each position a 6-0 silk suture was wound three turns on the ureter. Thus, a UUO model was prepared. Subsequently, the kidney was returned into the retroperitoneum, followed by skin suture. Then, the rat was kept in the same manner as before.

2-2. Cell Sheet Transplantation

Immediately after UUO, transplantation of the cell sheet was performed. From a fibrous capsule of the kidney of the five-week-old rat, a section having a length of about 1.5 cm and a width of about 0.8 cm was incised with microtweezers. Two pieces of the cell sheet for retaining renal functions were then transplanted onto the kidney. In order to compare effects of transplantation of a cell sheet with HGF production and those without HGF production, transplantation of a Met-5A cell sheet with or without having an HGF-producing function was performed. As a comparative example, an HGF-Met cell sheet was transplanted onto a fibrous capsule of a kidney, without removing the fibrous capsule.

2-3. Analysis by μCT (Cosmoscan GX, Rigaku)

After one, two, three, and four weeks, the rat was injected under anesthesia with 300 μL to 400 μL of a contrast medium (Omnipark 350, Daiichi Sankyo Company) from the caudal vein, for analysis of renal volume (v) by μCT specialized for small animals. From each of the resulting μCT images, the length of the kidney along the minor axis (x), the length thereof along the major axis (y), and the thickness thereof (z) were measured, which were then substituted into the following expression to calculate the volume.

$$v = 4/3 \pi \cdot x/2 \cdot y/2 \cdot z/2 \quad \text{[Expression 1]}$$

2-4. Analysis of Blood Flow Rate in Renal Artery

After a certain period, each animal under anesthesia was subjected to analysis on an echograph specialized for small animals (Vevo® 2100) to measure the radius of the renal artery, the heart rate, and the VTI (the velocity-time integral) on a PW mode. These parameters were substituted into the following expression to calculate the blood flow rate in the renal artery.

Blood flow rate (total amount of blood flowing through cross section of blood vessel per minute)=(sectional area of blood vessel)×(number of beats per minute)×(travelling distance of blood per beat) [Expression 2]

Sectional area of blood vessel: calculated from the diameter (2r) of the renal artery at a branched area measured by echography ($\pi \times r \times r$)

Number of beats per minute: the heart rate measured by simultaneously performed electrocardiography Travelling distance of blood per beat: a curve was drawn for the flow rate through the renal artery by PW, and the area defined by the base line and the curve between a telediastolic flow rate of one beat and that of the next beat was calculated (the area=the travelling distance of blood)

VTI: Velocity-time integral; measured on an echogram

2-5. Retrieval of Kidney

After UUO, the animal was kept for a certain period of time. The kidney was then perfusion fixed using 4% paraformaldehyde (PFA) for fixation (Muto Pure Chemicals, #33251) and retrieved. After the retrieved kidney was fixed with 4% PFA, fluid was sequentially replaced by alcohol, xylene, and paraffin to perform paraffin embedding. After paraffin embedding, the resulting kidney block was sliced into a thickness of about 3 μm. For preparation of a frozen slice, the kidney was fixed with 4% PFA, subjected to fluid replacement with a 30% sucrose PBS solution, made into a frozen block using an OTC compound, and then sliced into a thickness of 5 μm using a cryostat.

2-6. Histological Analysis

The paraffin slice was subjected to deparaffinization treatment, PAS staining, and HE staining, followed by morphology examination. The extent of fibrosis was evaluated by Sirius Red staining, by which collagen fibers were stained red. Myofibroblasts were detected as follows: the section was subjected to peroxidase blocking, then treated with αSMA antibody (clone 1A4, #M0851, DAKO), and subsequently stained brown by developing the color of DAB by DAKO envision. The resulting image was analyzed with image analysis software (Photo shop(registered trademark), Adobe Systems). Positive areas were selected based on the tones of color and then subjected to quantitative analysis with NIH Image J for comparison to the control groups. The transplanted cell sheet was visualized by staining using anti-SV40 antibody (Pab416, ab16879).

2-7. Checking HGF Production

HGF production by the cell sheet during culturing was quantitatively assessed by ELISA (R&D Systems). HGF production in a rat that had received transplantation was checked and detected by HGF immunostaining of the paraffin slice (using an antibody provided from Kanazawa University, see Yamada A, Mizuno S, Iwanari H et al. Rapid and sensitive enzyme linked immunosorbent assay for measurement of an HGF in rat and human tissues. Biomed. Res. 1995; 16:105-14.).

2-8. Checking Blood Vessel Structure

The frozen slice was subjected to blocking, followed by detection of vascular endothelial cells using anti-RECA1 antibody (Bio Rad). The secondary antibody used was an FITC-conjugated anti-mouse IgG antibody (Jackson ImmunoResearch Laboratories).

Example 1

Figure 2:
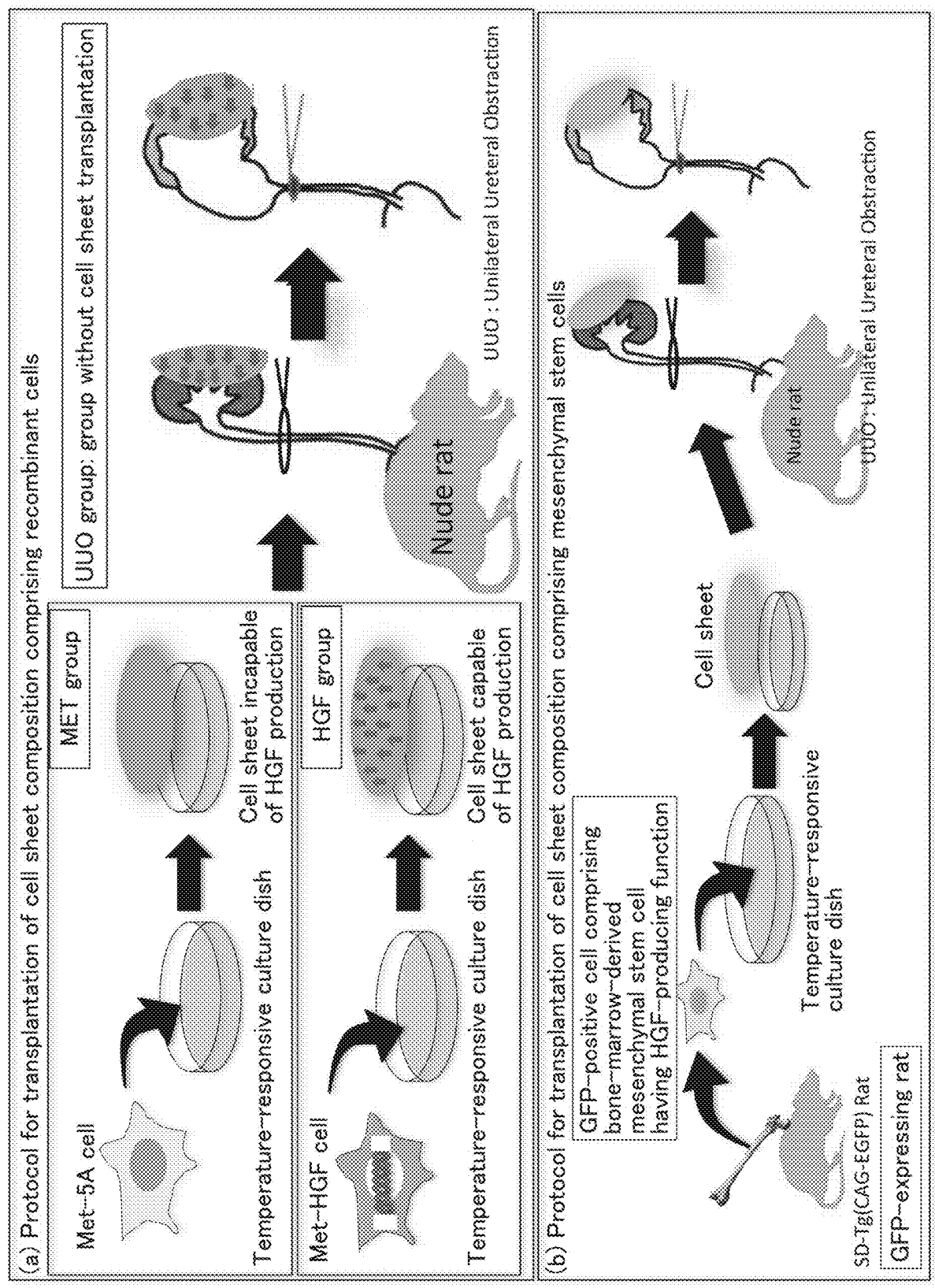
FIG. 2 illustrates a procedure for transplanting a cell sheet composition: (a) a protocol for confirming renal-function-retaining effects of a cell sheet genetically modified and given an HGF-producing function, in a UUO model; and (b) a protocol for confirming renal-function-retaining effects of a GFP-positive cell sheet comprising mesenchymal stem cells, in a UUO model.
Figure 3:
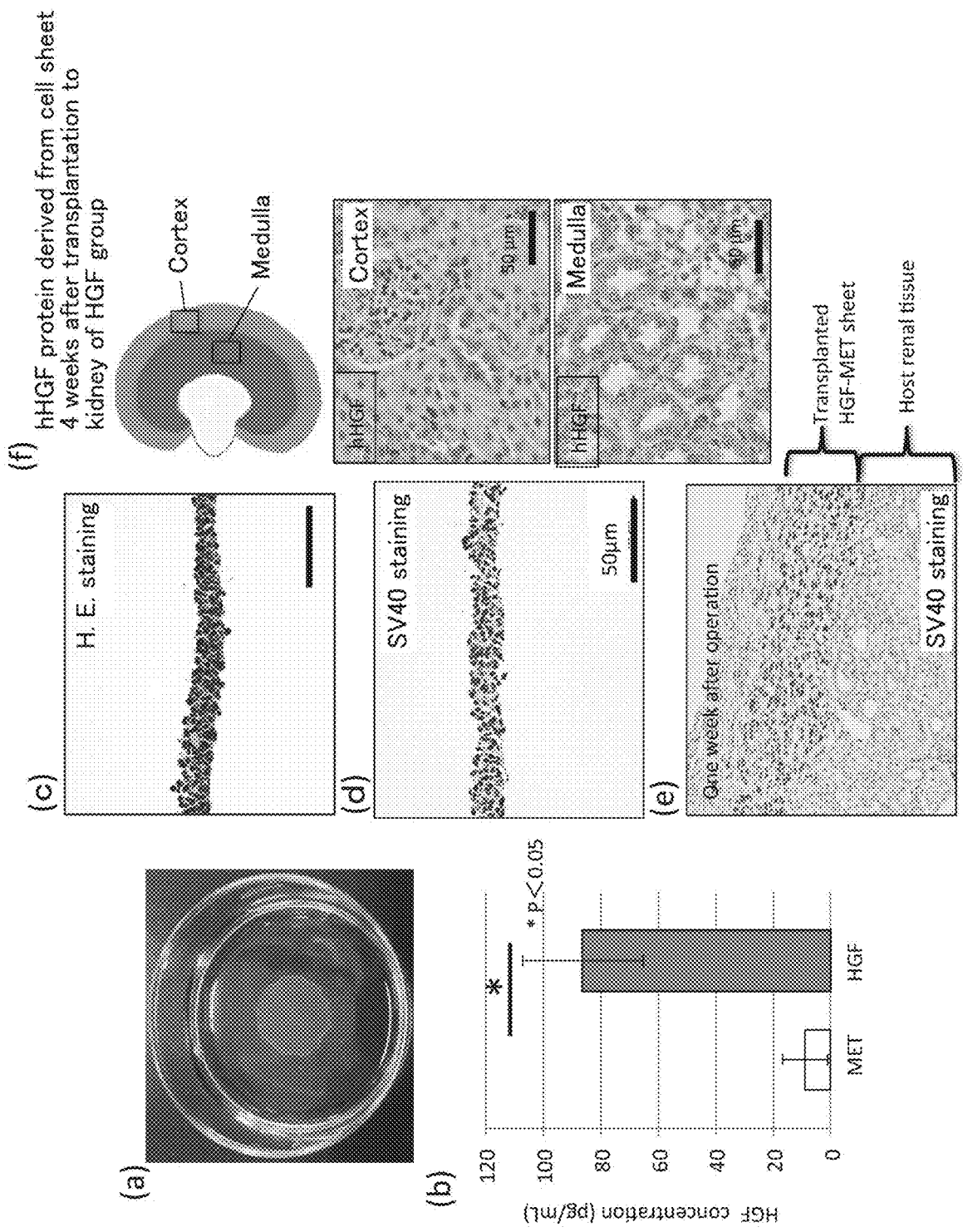
FIG. 3 illustrates HGF expression by a cell sheet genetically modified and given an HGF-expressing function, and the shape and the post-transplantation morphology of the sheet: (a) a MET-HGF cell sheet detached from a culture dish; (b) concentrations of an HGF secreted over 24 hours in the culture supernatant of the cell sheet; (c) HE staining of a cultured MET-HGF cell sheet; (d) SV40 proteins detected in a cultured MET-HGF cell sheet; (e) an SV40-positive MET-HGF cell sheet one week after transplantation thereof to the surface of a kidney under a fibrous capsule of the kidney; and (f) renal hHGF distribution in a group of transplanted rats with a MET-HGF cell sheet, measured four weeks after transplantation.

(1) Renal-Function-Retaining Effects of Cell Sheet Containing HGF-Gene Introduced Cells The experimental method is summarized in FIG. 2(a). The cell sheet genetically modified as above and given an HGF-producing function had an expression density of approximately 80 pg/mL/sheet within 24 hours (FIG. 3(b)). When harvested, the cell sheet was shrunk and stacked into two to three layers having a thickness of about 30 μm. The Met-5A cells and the Met-HGF cells used in this example were SV40-positive, and thus post-transplantation detection was performed by SV40 immunostaining (FIGS. 3(c) to 3(e)). Four weeks after transplantation onto the kidney, tissue staining was conducted using anti-hHGF antibody that had no cross-reactivity with rat HGF. Results evidently showed an hHGF distribution in the group transplanted with the cell sheet containing an HGF-producing function (FIG. 3(f)).

Figure 4:
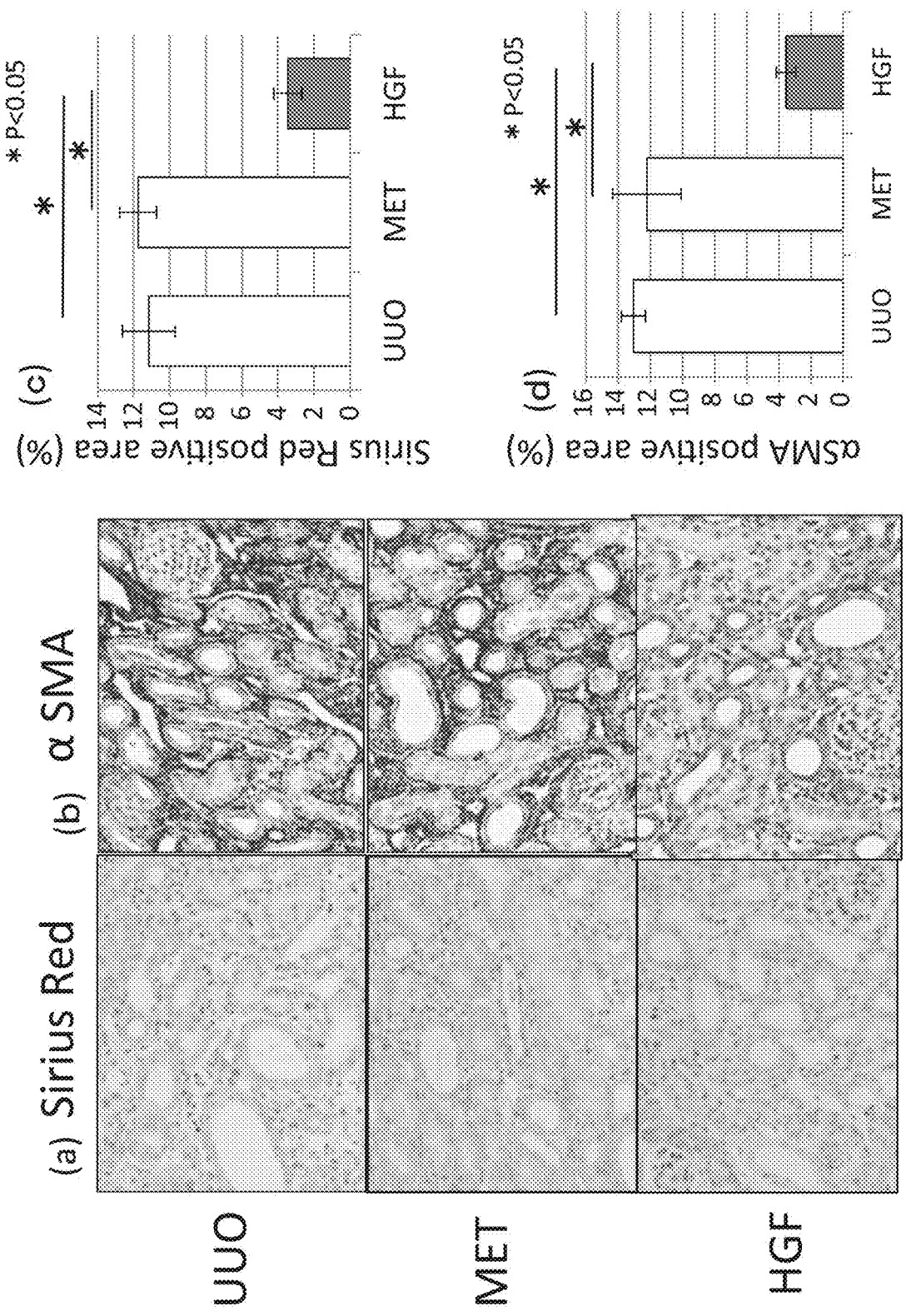
FIG. 4 illustrates results of histological analysis of a cell sheet having an HGF-expressing function, conducted one week after transplantation: (a) Sirius Red staining of fibrosis in a UUO group, a MET group, and an HGF group conducted one week after transplantation; (b) αSMA immunostaining of myofibroblasts in a UUO group, a MET group, and an HGF group conducted one week after transplantation; (c) a graph comparing the extents of fibrosis, obtained by quantification of images captured in experiments including (a); and (d) a graph comparing myofibroblast-positive areas, obtained by quantification of images captured in experiments including (b).

Histological analysis was performed one week after cell sheet transplantation. Results showed that the group transplanted with the HGF-producing cell sheet (HGF group) had a Sirius-Red-positive area (FIG. 4(c)) and an anti-SMA-positive area (FIG. 4(d)) significantly smaller than those of the group transplanted with a non-HGF-producing cell sheet (MET group) and of the group without cell sheet transplantation (UUO group), indicating that fibrosis was inhibited in the HGF group.

Figure 5:
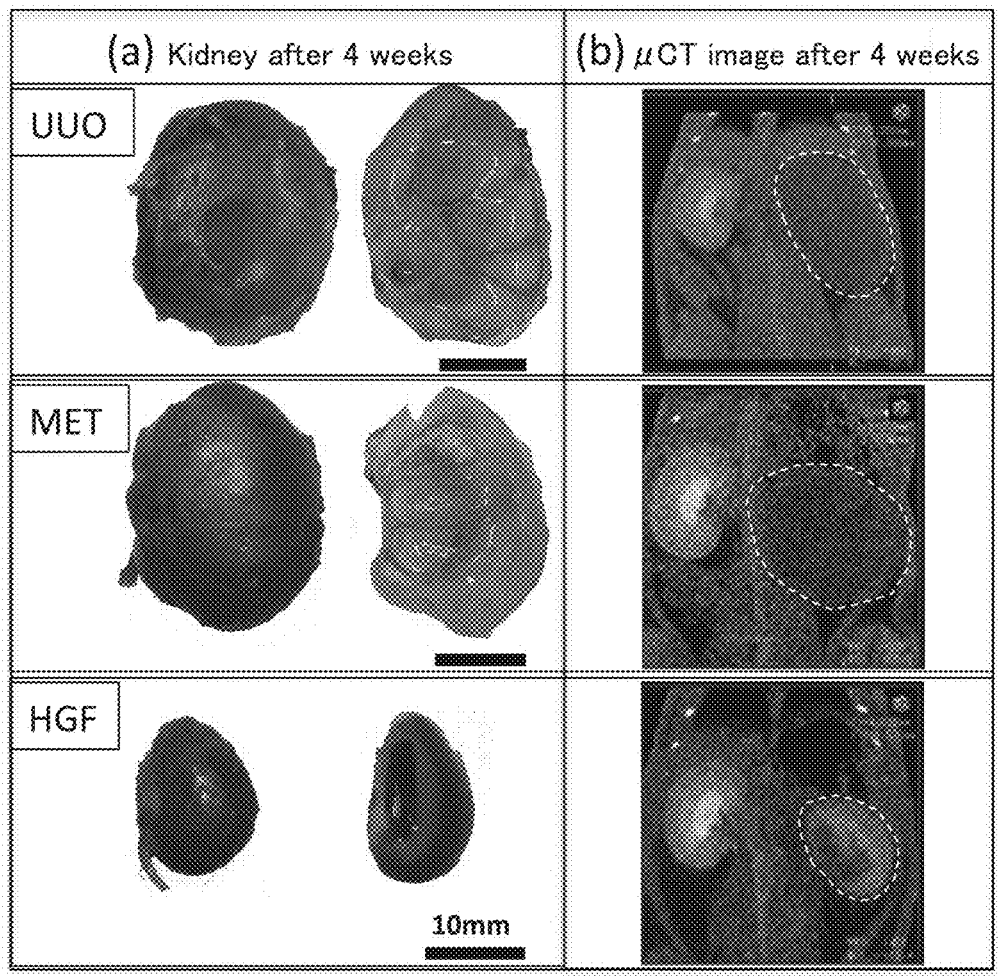
FIG. 5 illustrates changes in renal volume over four weeks after transplantation of a cell sheet having an HGF-expressing function, as well as images of kidneys captured four weeks after transplantation; (a) kidneys of a UUO group, a MET group, and an HGF group four weeks after transplantation; (b) μCT images of kidneys of a UUO group, a MET group, and an HGF group captured four weeks after transplantation; and (c) a graph illustrating the time courses of changes in renal volume calculated from analysis in (b). A cell sheet having an HGF-expressing function was applied on a fibrous capsule of a kidney ("HGF (on capsule)").
Figure 5:
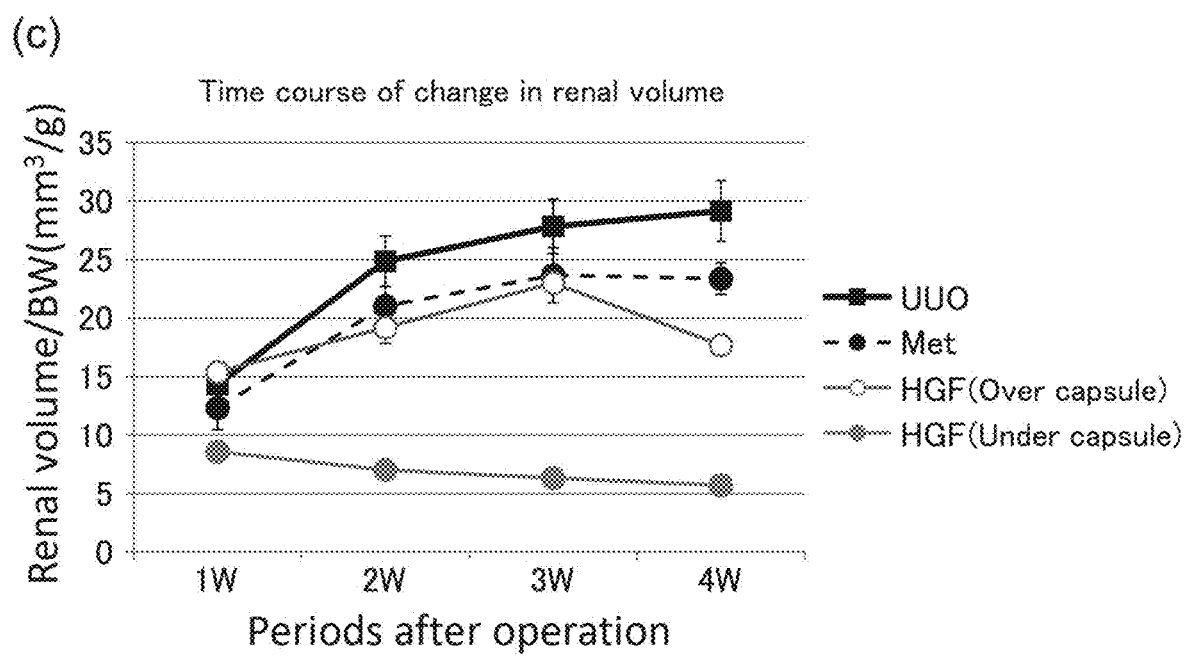

Four weeks after UUO model preparation, changes in volumes and appearances of the kidneys were compared between the groups. Results showed that the UUO group and the MET group had renal volumes increased four weeks after UUO preparation (FIG. 5(c)). Each of the UUO group and the MET group also showed collapse of the renal medullary structure and thinning of the renal cortex as is evident from the sectional views (FIG. 5(a), right), as well as a remarkably swollen kidney (FIGS. 5(a) to 5(c)). In the HGF group, the renal volume did not change much four weeks after UUO preparation (FIG. 5) indicating reduced collapse of the renal medullary structure and thinning of the renal cortex. These effects were observed only in an HGF-producing cell sheet transplanted on the surface of the kidney under a fibrous capsule of the kidney, but not observed in the group in which a fibrous capsule was not removed and the sheet was transplanted onto the fibrous capsule (FIG. 5(c): HGF (transplanted onto fibrous capsule)). These results showed that the HGF-producing cell sheet transplanted on the surface of the kidney under a fibrous capsule of the kidney remarkably inhibited collapse of the renal medullary structure and the resulting thinning of the renal cortex from being caused by UUO and also remarkably inhibited an increase in the renal volume from being caused by pressure applied by urine, confirming the renal-medulla-retaining effects.

Figure 6:
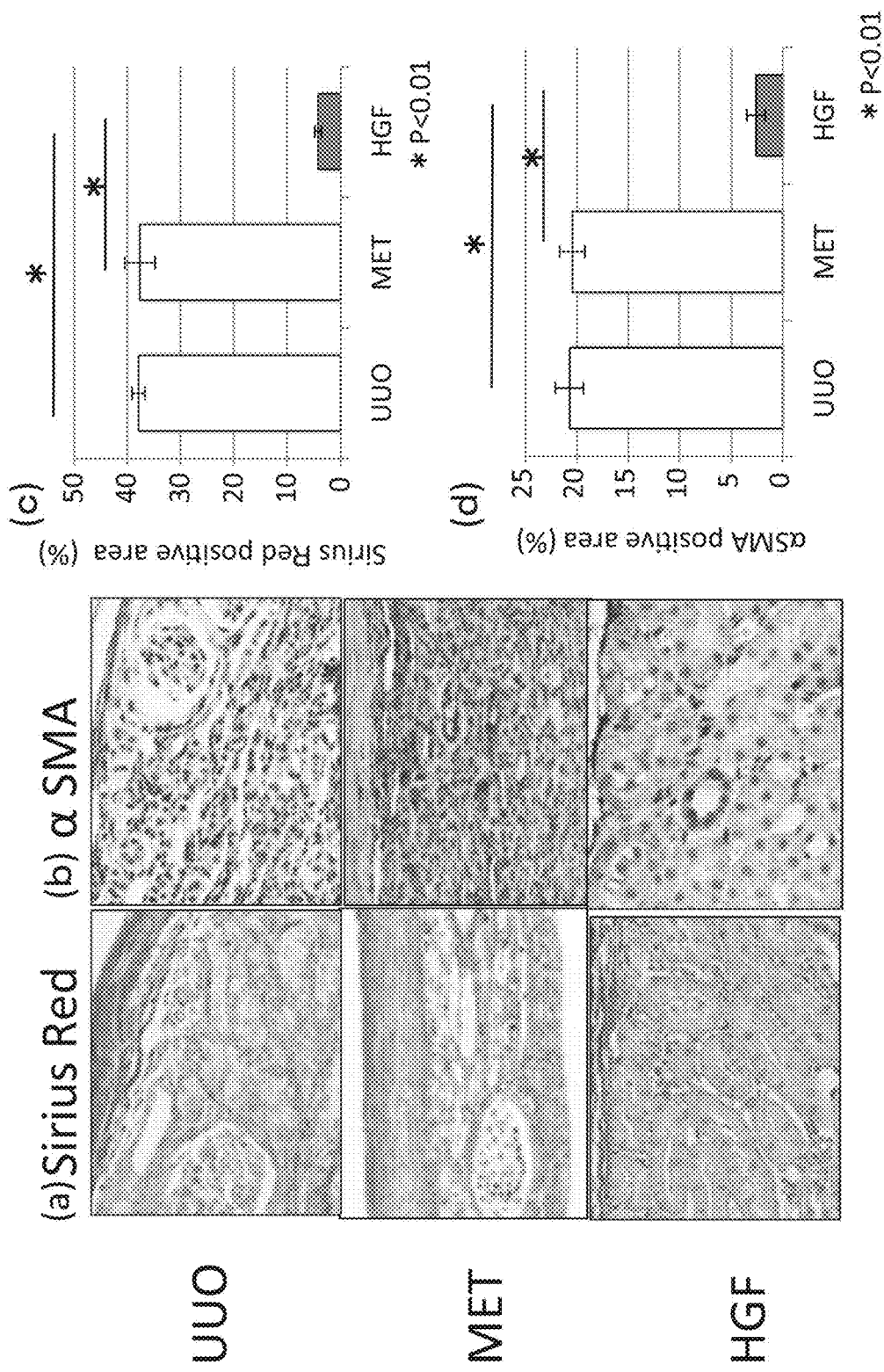
FIG. 6 illustrates histological analysis of a cell sheet having an HGF-expressing function, conducted four weeks after transplantation: (a) Sirius Red staining of fibrosis in UUO, MET, and HGF groups conducted four weeks after transplantation; (b) αSMA immunostaining of myofibroblasts in UUO, MET, and HGF groups conducted four weeks after transplantation; (c) a graph comparing the extents of fibrosis, obtained by quantification of images captured in experiments including (a); and (d) a graph comparing myofibroblast-positive areas, obtained by quantification of images captured in experiments including (b).

Results of histological analysis performed four weeks after cell sheet transplantation are shown in FIG. 6. FIG. 6 clearly demonstrates that fibrosis was inhibited in the HGF group.

Figure 7:
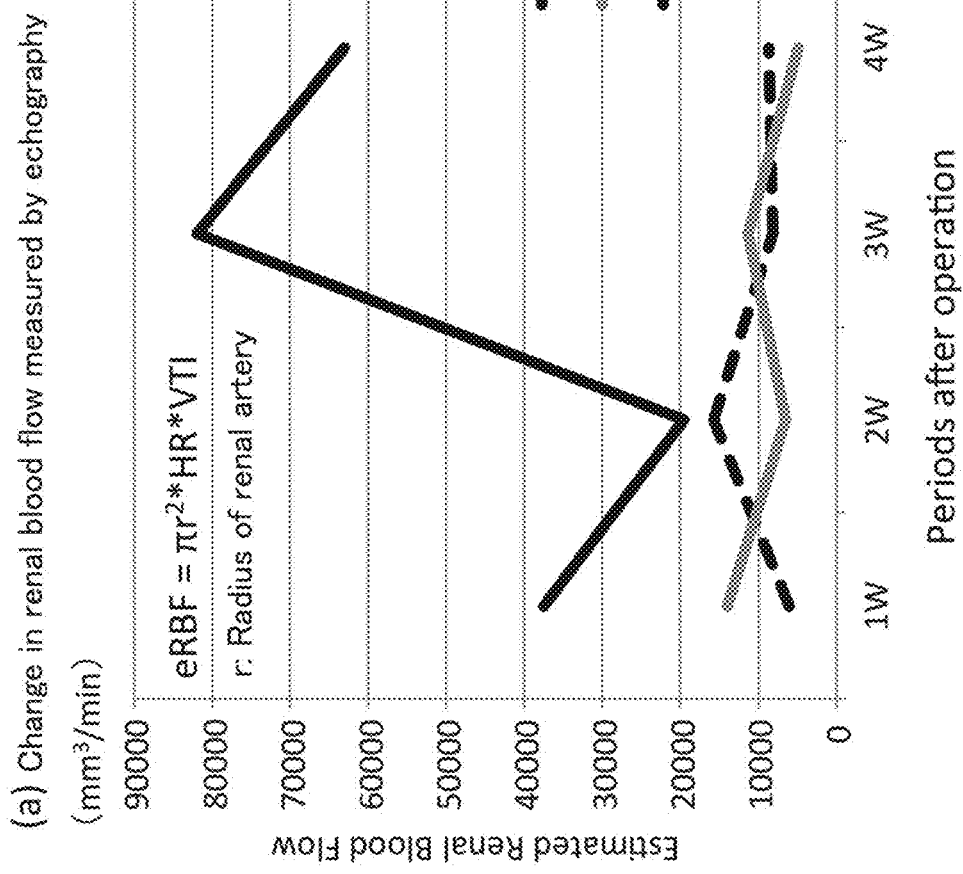
FIG. 7 illustrates echographic analysis of blood flow and analysis of blood vessel structure of rats transplanted with a cell sheet having an HGF-expressing function: (a) a graph illustrating changes in renal blood flow rate of rats measured by echography specialized for small animals; and (b) images of vascular endothelial cells in a MET group and an HGF group stained four weeks after transplantation.

The blood flow and the blood vessel structure were also analyzed by echography. The echographic analysis of blood flow rate demonstrates that the HGF group had a high blood flow rate over four weeks compared to that of the control groups (the UUO group and the MET group) (FIG. 7(a)). The analysis also demonstrates that the HGF group highly maintained the blood vessel structure compared to the control groups (FIG. 7(b)).

Example 2

(2) Renal-Function-Retaining Effects of Mesenchymal Stem Cell Sheet

Figure 8:
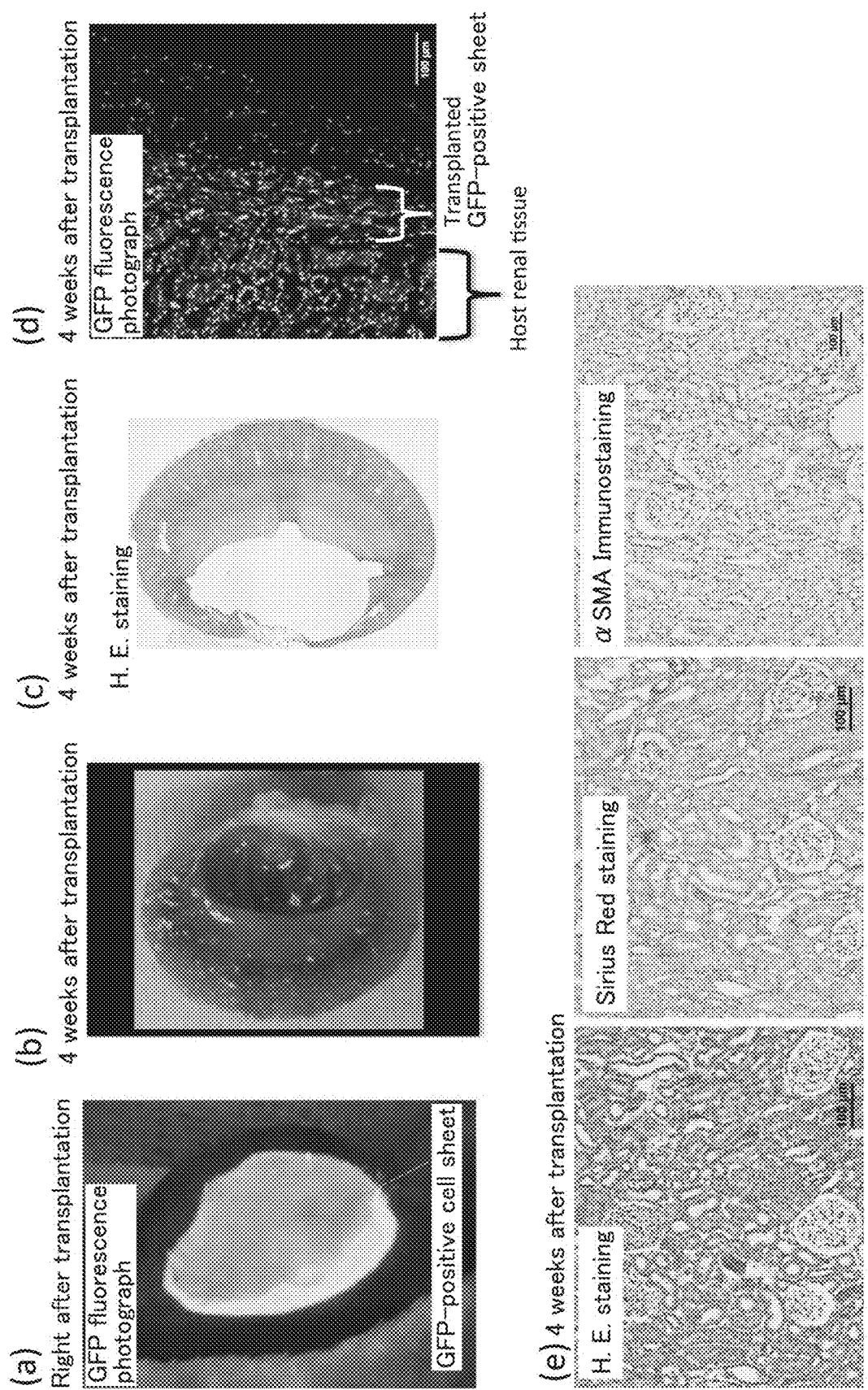
FIG. 8 illustrates results of kidney tissue analysis conducted four weeks after transplantation of a cell sheet comprising mesenchymal stem cells: (a) a GFP-positive cell sheet comprising bone-marrow-derived mesenchymal stem cells right after transplantation thereof onto a kidney surface; (b) a kidney four weeks after transplantation of a GFP-positive cell sheet comprising bone-marrow-derived mesenchymal stem cells; (c) HE staining of renal tissue conducted four weeks after transplantation of a GFP-positive cell sheet comprising bone-marrow-derived mesenchymal stem cells; (d) a GFP-positive cell sheet comprising bone-marrow-derived mesenchymal stem cells four weeks after transplantation; and (e) HE staining, Sirius Red staining, and αSMA immunostaining of renal tissue conducted four weeks after transplantation of a GFP-positive cell sheet comprising bone-marrow-derived mesenchymal stem cells.

A GFP-positive cell sheet comprising bone-marrow-derived mesenchymal stem cells was transplanted into a UUO model in accordance with the procedure described above. As shown in FIG. 8, transplantation of the GFP-positive cell sheet comprising bone-marrow-derived mesenchymal stem cells remarkably inhibited collapse of the renal medullary structure and the resulting thinning of the renal cortex caused by UUO and also remarkably inhibited an increase in the renal volume caused by pressure applied by urine, just like in Example 1. Thus, the renal-medulla-retaining effects were confirmed.

Traditionally, administration of an HGF into blood and gene transfer of an HGF have been studied because the HGF has action to inhibit TGF-β-attributable renal fibrosis. However, a report (NPL 3) indicates that the systemic administration thereof such as intravenous administration has little action on a kidney because most of the HGF dose is lost by first-pass effect in the liver. In the present invention, a cell sheet comprising mesenchymal stem cells that have an HGF-producing function is prepared and then directly transplanted onto a surface layer of a kidney, for the purpose of long-term administration of an HGF locally and persistently to the kidney. A nephropathy model prepared by unilateral ureteral obstruction was examined four weeks after preparation thereof. Results showed that the transplantation of the cell sheet having an HGF-producing function alleviated vascular insufficiency occurring in the renal medulla due to renal disorder and retained the structure of renal tubules in the renal medulla, in which the renal tubules are responsible for urine concentration or water reabsorption (the most important renal function), regulation of electrolyte concentrations and pH in a living organism, and reabsorbance of proteins and amino acids. Thus, unprecedented renal-function-retaining effects have been achieved.

REFERENCE TO A "SEQUENCE LISTING" SUBMITTED AS ASCII TEXT FILES VIA EFS-WEB

The Sequence Listing written in file 093803-003800US-1036967_SequenceListing.txt created on Jan. 25, 2017, 6,189 bytes, machine format IBM-PC, MS-Windows operating system, submitted via ASCII text file via EFS-Web, in accordance with 37 C.F.R. §§ 1.821- to 1.825, is hereby incorporated by reference in its entirety for all purposes.

The invention claimed is:

1. A method of inhibiting progression of a renal disorder, wherein the renal disorder is selected from group consisting of fibrosis of the renal cortex, collapse of the renal medullary structure, degradation of renal medullary functions, and thinning of the renal parenchyma, in a subject in need of treatment of the renal disorder, the method comprising:
    (i) preparing a single- or multi-layered cell sheet composition with a culture of cells that have a function of producing a hepatocyte growth factor (HGF), wherein the cells comprise a recombinant vector having a nucleic acid encoding an HGF protein, or mesenchymal stem cells that have a function of producing HGF;
    (ii) peeling off or removing at least one part of a fibrous capsule of a kidney; and
    (iii) applying the single- or multi-layered cell sheet composition to a surface of the kidney where the at least one part of the fibrous capsule has been peeled off or removed, wherein production of HGF inhibits progression of the renal disorder.

2. The method according to claim 1, wherein the renal disorder results from one or more kidney diseases selected from the group consisting of diabetic nephropathy, nephrosclerosis, chronic glomerulonephritis, IgA nephropathy, obstructive nephropathy, rapidly progressive glomerulonephritis, lupus nephritis, interstitial nephritis, and post-kidney-transplantation nephropathy.

3. The method according to claim 1, wherein the mesenchymal stem cells are derived from cord blood, placenta, bone marrow, adipose tissue, a synovial membrane, dental pulp, and/or pluripotent stem cells.

4. The method according to claim 1, wherein the mesenchymal stem cells are derived from bone marrow.

5. The method according to claim 1, wherein the single- or multi-layered cell sheet composition is prepared by cell sheet-preparing steps, comprising:
    (1) seeding the culture of cells on a stimulus-responsive cell culture substrate and culturing the cells to confluency; and (2) giving the stimulus-responsive cell culture substrate a stimulus to induce detachment of the cells from the substrate.

6. The method according to claim 5, wherein a medium used in culturing in step (1) contains ascorbic acid or a salt thereof.

* * * * *

SEQUENCE LISTING

```
<160> NUMBER OF SEQ ID NOS: 1

<210> SEQ ID NO 1
<211> LENGTH: 728
<212> TYPE: PRT
<213> ORGANISM: Homo sapiens

<400> SEQUENCE: 1

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
```

```
                    20              25              30
Arg Lys Arg Arg Asn Thr Ile His Glu Phe Lys Lys Ser Ala Lys Thr
                35              40              45

Thr Leu Ile Lys Ile Asp Pro Ala Leu Lys Ile Lys Thr Lys Lys Val
    50              55              60

Asn Thr Ala Asp Gln Cys Ala Asn Arg Cys Thr Arg Asn Lys Gly Leu
65              70              75              80

Pro Phe Thr Cys Lys Ala Phe Val Phe Asp Lys Ala Arg Lys Gln Cys
                85              90              95

Leu Trp Phe Pro Phe Asn Ser Met Ser Ser Gly Val Lys Lys Glu Phe
                100             105             110

Gly His Glu Phe Asp Leu Tyr Glu Asn Lys Asp Tyr Ile Arg Asn Cys
                115             120             125

Ile Ile Gly Lys Gly Arg Ser Tyr Lys Gly Thr Val Ser Ile Thr Lys
                130             135             140

Ser Gly Ile Lys Cys Gln Pro Trp Ser Ser Met Ile Pro His Glu His
145             150             155             160

Ser Phe Leu Pro Ser Ser Tyr Arg Gly Lys Asp Leu Gln Glu Asn Tyr
                165             170             175

Cys Arg Asn Pro Arg Gly Glu Glu Gly Gly Pro Trp Cys Phe Thr Ser
                180             185             190

Asn Pro Glu Val Arg Tyr Glu Val Cys Asp Ile Pro Gln Cys Ser Glu
                195             200             205

Val Glu Cys Met Thr Cys Asn Gly Glu Ser Tyr Arg Gly Leu Met Asp
    210             215             220

His Thr Glu Ser Gly Lys Ile Cys Gln Arg Trp Asp His Gln Thr Pro
225             230             235             240

His Arg His Lys Phe Leu Pro Glu Arg Tyr Pro Asp Lys Gly Phe Asp
                245             250             255

Asp Asn Tyr Cys Arg Asn Pro Asp Gly Gln Pro Arg Pro Trp Cys Tyr
                260             265             270

Thr Leu Asp Pro His Thr Arg Trp Glu Tyr Cys Ala Ile Lys Thr Cys
                275             280             285

Ala Asp Asn Thr Met Asn Asp Thr Asp Val Pro Leu Glu Thr Thr Glu
                290             295             300

Cys Ile Gln Gly Gln Gly Glu Gly Tyr Arg Gly Thr Val Asn Thr Ile
305             310             315             320

Trp Asn Gly Ile Pro Cys Gln Arg Trp Asp Ser Gln Tyr Pro His Glu
                325             330             335

His Asp Met Thr Pro Glu Asn Phe Lys Cys Lys Asp Leu Arg Glu Asn
                340             345             350

Tyr Cys Arg Asn Pro Asp Gly Ser Glu Ser Pro Trp Cys Phe Thr Thr
                355             360             365

Asp Pro Asn Ile Arg Val Gly Tyr Cys Ser Gln Ile Pro Asn Cys Asp
                370             375             380

Met Ser His Gly Gln Asp Cys Tyr Arg Gly Asn Gly Lys Asn Tyr Met
385             390             395             400

Gly Asn Leu Ser Gln Thr Arg Ser Gly Leu Thr Cys Ser Met Trp Asp
                405             410             415

Lys Asn Met Glu Asp Leu His Arg His Ile Phe Trp Glu Pro Asp Ala
                420             425             430

Ser Lys Leu Asn Glu Asn Tyr Cys Arg Asn Pro Asp Asp Asp Ala His
                435             440             445
```

-continued

```
Gly Pro Trp Cys Tyr Thr Gly Asn Pro Leu Ile Pro Trp Asp Tyr Cys
    450                 455                 460
Pro Ile Ser Arg Cys Glu Gly Asp Thr Thr Pro Thr Ile Val Asn Leu
465                 470                 475                 480
Asp His Pro Val Ile Ser Cys Ala Lys Thr Lys Gln Leu Arg Val Val
                485                 490                 495
Asn Gly Ile Pro Thr Arg Thr Asn Ile Gly Trp Met Val Ser Leu Arg
                500                 505                 510
Tyr Arg Asn Lys His Ile Cys Gly Gly Ser Leu Ile Lys Glu Ser Trp
            515                 520                 525
Val Leu Thr Ala Arg Gln Cys Phe Pro Ser Arg Asp Leu Lys Asp Tyr
    530                 535                 540
Glu Ala Trp Leu Gly Ile His Asp Val His Gly Arg Gly Asp Glu Lys
545                 550                 555                 560
Cys Lys Gln Val Leu Asn Val Ser Gln Leu Val Tyr Gly Pro Glu Gly
                565                 570                 575
Ser Asp Leu Val Leu Met Lys Leu Ala Arg Pro Ala Val Leu Asp Asp
                580                 585                 590
Phe Val Ser Thr Ile Asp Leu Pro Asn Tyr Gly Cys Thr Ile Pro Glu
            595                 600                 605
Lys Thr Ser Cys Ser Val Tyr Gly Trp Gly Tyr Thr Gly Leu Ile Asn
    610                 615                 620
Tyr Asp Gly Leu Leu Arg Val Ala His Leu Tyr Ile Met Gly Asn Glu
625                 630                 635                 640
Lys Cys Ser Gln His His Arg Gly Lys Val Thr Leu Asn Glu Ser Glu
                645                 650                 655
Ile Cys Ala Gly Ala Glu Lys Ile Gly Ser Gly Pro Cys Glu Gly Asp
                660                 665                 670
Tyr Gly Gly Pro Leu Val Cys Glu Gln His Lys Met Arg Met Val Leu
            675                 680                 685
Gly Val Ile Val Pro Gly Arg Gly Cys Ala Ile Pro Asn Arg Pro Gly
    690                 695                 700
Ile Phe Val Arg Val Ala Tyr Tyr Ala Lys Trp Ile His Lys Ile Ile
705                 710                 715                 720
Leu Thr Tyr Lys Val Pro Gln Ser
                725
```